United States Patent
Kumoi et al.

(10) Patent No.: US 6,896,865 B2
(45) Date of Patent: May 24, 2005

(54) METHOD FOR RECOVERING HYDROGEN CHLORIDE FROM CHLORINE BASED WASTE AND USE OF RECOVERED HYDROGEN CHLORIDE

(75) Inventors: Sadakatsu Kumoi, Hikari (JP); Kouya Honjoh, Shinnanyo (JP); Tsugio Murakami, Shinnanyo (JP)

(73) Assignee: Tosoh Corporation, Yamaguchi-Ken (JP)

( * ) Notice: Subject to any disclaimer, the term of this patent is extended or adjusted under 35 U.S.C. 154(b) by 308 days.

(21) Appl. No.: 09/842,136

(22) Filed: Apr. 26, 2001

(65) Prior Publication Data

US 2001/0038818 A1 Nov. 8, 2001

(30) Foreign Application Priority Data

Apr. 28, 2000 (JP) ...................................... P2000-134264

(51) Int. Cl.[7] ................................................. C01B 7/07
(52) U.S. Cl. ........................ 423/488; 423/241; 588/206; 588/208
(58) Field of Search ................................ 423/488, 481, 423/240 R, 241; 588/205, 206, 207, 208

(56) References Cited

U.S. PATENT DOCUMENTS 5,000,858 A * 3/1991 Manning et al. ............. 210/709
5,026,535 A * 6/1991 Jonsson et al. .............. 423/525

FOREIGN PATENT DOCUMENTS

| EP | 0619268 A1 | 10/1994 |
|----|------------|---------|
| JP | 6-180104 | 6/1994 |
| JP | 8-267049 | 10/1996 |
| JP | 11-80746 | 3/1999 |
| JP | 11-158319 | 6/1999 |
| JP | 11-286687 | 10/1999 |

* cited by examiner

*Primary Examiner*—N M. Nguyen
(74) *Attorney, Agent, or Firm*—Steven B. Kelber; DLA Piper Rudnick Gray Cary US LLP

(57) ABSTRACT

To provide a process for recovering high quality hydrogen chloride rationally with good economical efficiency, particularly hydrogen chloride with an elevated quality level to be provided as the feedstock for the oxychlorination reaction in producing dichloroethane and a vinyl chloride monomer from a hydrogen chloride gas to be generated by the combustion of chlorine based waste. To use a process for recovering hydrogen chloride from chlorine based waste comprises adding water and a reducing agent to an acid gas obtained by the combustion of chlorine based waste to effect reaction to obtain a crude hydrogen chloride aqueous solution having an oxidation-reduction potential of not higher than 900 mV and then, distilling the crude hydrogen chloride aqueous solution to obtain a purified hydrogen chloride gas.

11 Claims, No Drawings

METHOD FOR RECOVERING HYDROGEN CHLORIDE FROM CHLORINE BASED WASTE AND USE OF RECOVERED HYDROGEN CHLORIDE

BACKGROUND OF THE INVENTION

The present invention relates to a method for recovering hydrogen chloride from chlorine based waste, and more specifically, it relates to a process for recovering high quality hydrogen chloride from an acid gas generated by the combustion of chlorine based solid waste such as polyvinyl chloride, polyvinylidene chloride and chloroprene rubber and chlorine based waste containing organic chlorine compounds such as a chlorine based organic waste liquor to be discharged from plants for producing a vinyl chloride monomer, dichlorobutene, chlorobenzene and the like.

Organic chlorine compounds have such a number of excellent properties that they are stable with reduced deterioration and further, easily available and economical and accordingly, polyvinyl chloride representing them is being used in a large quantity all over the world. However, its used material is simultaneously generated in a large quantity and further, chlorine based organic waste liquors are generated at the time of its production. On that account, from the standpoint of preservation of environment and effective utilization of resources, the technology of treatment of these types of waste is demanded from all angles and a number of proposals have been made.

For example, Japanese Patent Publication (Kokai) No. Hei 8-267049/1996 discloses a method for subjecting waste containing chlorine based polymeric compounds to heat treatment, allowing the generated hydrogen chloride gas to be absorbed in water, neutralizing the resulting hydrogen chloride aqueous solution with an alkali agent such as sodium hydroxide and calcium hydroxide and evaporating water to obtain a chloride. This technique is comparatively simple and can render hydrogen chloride harmless. However, it uses a large amount of a useful alkali agent in neutralizing hydrogen chloride and consumes much energy in evaporating water and thus, is not economical and, in addition, the recovered product is a chloride whose value added has not been high.

Japanese Patent Publication (Kokai) No. Hei 11-286687/1999 discloses a method for obtaining carbides and a hydrogen chloride gas by thermal decomposition of chlorine-containing plastics. It is shown that the carbon component in the waste is formed into carbides which can be used as the fuel of cement and the like and the chlorine component is formed into hydrogen chloride which can be used as the feedstock in the oxychlorination reaction of ethylene with hydrochloric acid and thus, this method is reasonable. However, the dechlorination treatment at the time of thermal decomposition is not complete and as the result, part of chlorine remains in the carbides and there is a fear of material corrosion and product contamination by the chlorine to be generated in use and its migration into a discharged gas and further, floating foreign substances derived from the carbides, carbon monoxide, a carbon dioxide gas, a sulfurous gas, and sometimes, foreign gaseous components such as a chlorine gas are present in the recovered hydrogen chloride and accordingly, these substances have had to be purified and removed in some cases.

Japanese Patent Publication (Kokai) No. Hei 11-158319/1999 discloses a method of heating waste plastics containing polyvinyl chloride and plasticizers to obtain an organic solid substance and a hydrogen chloride gas and, in the purification of the resulting hydrogen chloride gas, cooling the resulting hydrogen chloride gas to separate the plasticizers, allowing the cooled gas to be absorbed in water to form hydrochloric acid and then, allowing organic components in the hydrochloric acid adsorbed on active carbon to remove them. According to this method the quality of hydrochloric acid can considerably be improved to broaden its use. However, a large amount of active carbon is necessary and its regeneration is difficult and thus, this method is not economical. In addition, the adsorption capacity of active carbon of inorganic substances and hydro-philic low molecular weight organic substances are small and thus, the quality of the obtained hydrochloric acid could not be said sufficient. Further, the organic solids are expected to be utilized as fuels but they contain a chlorine component which sometimes has to be purified and eliminated in use.

Japanese Patent Publication (Kokai) No. Hei 11-80746/1999 discloses a method for recovering high purity hydrochloric acid which comprises thermally decomposing waste plastics containing polyvinyl chloride to obtain a solid or liquid fuel and a hydrogen chloride gas, allowing the resulting hydrogen chloride gas to be absorbed in water to obtain hydrochloric gas, adding hydrogen peroxide to this hydrochloric acid to decompose and remove organic substances. However, the oxidative decomposition of organic substances by hydrogen peroxide does not have much effect on high molecular weight organic substances, and the action of removing inorganic substances is not much expected. Further, in addition to the cost of hydrogen peroxide, generation of a chlorine gas by hydrogen peroxide is anticipated and thus, the quality of hydrochloric acid could not be said sufficient.

The target component to be dealt with by the combustion of chlorine based waste is a chlorine gas. Its concentration varies depending on the combustion conditions, and the chlorine gas to be generated relates to corrosion of the equipment and as the countermeasure, Japanese Patent Publication (Kokai) No. Hei 6-180104/1994 discloses a method for preventing the corrosion of equipment by injecting a sulfurous acid gas into a combustion gas of a chlorine-containing fuel. This method is effective for anticorrosion of equipment but unreacted sulfurous acid gas and the sulfuric acid mist formed by reaction accompany a hydrogen chloride gas and are absorbed in water to come to sulfuric acid and sulfurous acid to bring about reduction in the quality of hydrochloric acid. Further, the absorption efficiency of unreacted sulfurous acid gas into water is low and thus, the sulfurous acid gas migrates from absorption equipment into a discharged gas and as the result, there is a fear of causing air pollution. Further, this Patent Publication does not show the purification of the hydrogen chloride gas and hydrochloric acid.

SUMMARY OF THE INVENTION

All above described techniques are methods of subjecting chlorine based waste to heat treatment to render the chlorine content in the waste a hydrogen chloride gas. Hydrogen chloride is an important basic chemical raw material to be used in a wide range of fields as an alkali neutralizing agent, a feedstock in the production of a vinyl chloride monomer by the oxychlorination reaction method, an acid detergent for steel, an electricity/semiconductor-related etchant and the like.

In order to broaden the utilization range of this hydrogen chloride to enhance its value added, the improvement of the quality of hydrogen chloride is essential. However, the gas component to be generated in heating chlorine based waste contains carbon monoxide (CO), sulfur oxides ($SO_x$), nitrogen oxides ($NO_x$), chlorine ($Cl_2$), volatile organic substances and furthermore, floating dust and the like at different concentrations depending on the combustion conditions in addition to water ($H_2O$) and a carbon dioxide gas ($CO_2$) to be generated by combustion. Accordingly, in order to obtain high quality hydrogen chloride which does not substantially contain foreign substances from a hydrogen chloride gas to be generated by combustion, it is necessary to effectively and efficiently eliminate these foreign substances. In this respect, all above described prior art techniques are not satisfactory.

The object of the present invention is to overcome the prior art problems to provide a process for recovering high quality hydrogen chloride reasonably with good economical efficiency, particularly hydrogen chloride with an elevated quality level to be provided as the feedstock for the oxychlorination reaction in the production of dichloroethane and a vinyl chloride monomer from a hydrogen chloride gas to be generated by the combustion of chlorine based waste.

DETAILED DESCRIPTION OF THE INVENTION

In order to solve these prior art problems, the present inventors have strenuously investigated methods for treating a hydrogen chloride gas to be generated by the combustion of chlorine based waste.

As the result, it has been found that by (1) allowing a hydrogen chloride gas in an acid gas generated upon combustion to be once absorbed in water to obtain a crude hydrogen chloride aqueous solution; (2) creating a reductive atmosphere by adding a reducing agent to the crude hydrogen chloride aqueous solution in such an amount so as to render its oxidation-reduction potential not higher than 900 mV; and then, (3) distilling the crude hydrogen chloride aqueous solution to obtain a purified hydrogen chloride gas, foreign components in the combustion gas can effectively be eliminated to recover high quality hydrogen chloride which can be provided as the feedsock for the oxychlorination reaction in the production of dichloroethane and a vinyl chloride monomer, and the present invention has been completed.

Namely, the present invention is a method for recovering hydrogen chloride from chlorine based waste which comprises adding water and a reducing agent to an acid gas obtained by the combustion of chlorine based waste to effect reaction to obtain a crude hydrogen chloride aqueous solution having an oxidation-reduction potential of not higher than 900 mV and then, distilling the crude hydrogen chloride aqueous solution to obtain a purified hydrogen chloride gas.

The present invention will now be explained in detail.

The chlorine based waste in the present invention is not particularly limited and its major target is, for example, known chlorine-containing solid waste and chlorine-containing liquid waste such as a chlorine-containing organic waste liquor. For example, the solid chlorine-containing waste includes chlorine-containing polymeric compounds such as polyvinyl chloride, polyvinylidene chloride, chlorinated polyethylene and chloroprene rubber, and the liquid waste includes, for example, a waste liquor to be discharged mainly in the distillation step in the plants for the production of ethylene dichloride, a vinyl chloride monomer, dichlorobutene, chlorobenzene, benzyl chloride, chlorohydrin and the like.

The solid waste to be applied can be either in an indeterminate or block or in the form of sheets, plates, pipes, bars or the like but it is preferred that the solid waste to be provided for combustion is rendered small pieces by means of cutting, pulverization and the like or formed into a slurry by mixing with liquid waste before combustion. In the case of rendering the solid waste small pieces, such small pieces preferably have a size of from 1 up to about 50 mm, more preferably a size of from 2 up to 5 mm, and with these small pieces, the solid waste can be provided for combustion with good handling. The liquid waste can be provided for combustion as such or in the form of a mixture with a fuel such as a heavy oil and kerosine. And in the present invention, the target contains a mixture of above-mentioned solid waste and liquid waste.

In the process of the present invention, the above described chlorine based waste is subjected to combustion. The combustion equipment to be used in combustion is not particularly limited, and any of a rotary kiln system, a fluidized bed system, a vertical air flow incinerator, a horizontal air flow incinerator and the like can suitably be employed. Of them, when the solid waste is subjected to complete combustion, the vertical air flow incinerator and the fluidized bed system are preferred, when the solid waste is thermally decomposed to obtain carbides as fuels, the rotary kiln system is preferred, and when the liquid waste is subjected to combustion, the horizontal incinerator is preferred.

As the conditions of combustion, it is preferred that in incinerating the waste, a sufficient amount of air or oxygen is supplied to preferably render the concentration of oxygen in the combustion gas typically 2 to 15% by volume and in obtaining carbides, the chlorine based waste is subjected to combustion by indirect heating or with heated nitrogen or it is subjected to partial combustion in an atmosphere rather insufficient in air or oxygen. The temperature of combustion varies depending on the decomposition temperature of the waste or whether or not to obtain carbides and cannot absolutely be said but in obtaining a carbide from polyvinyl chloride as the waste, the temperature is typically in the range of 250 to 350° C., and in incinerating a chlorine based liquor to be discharged from a vinyl chloride monomer production plant is typically in the range of 500 to 1,500° C.

The acid gas to be obtained by combustion contains, in addition to hydrogen chloride, CO, $CO_2$, $SO_x$ and further, $Cl_2$, $NO_x$, and the like which are oxidative gases and, in addition, water vapor and $N_2$ and $O_2$ derived from air, volatile organic substances and moreover, fine powdered carbides and floating foreign substances such as inorganic compounds. The composition of these components differs depending on the type of the feedstock chlorine based waste, the amount of burning accelerating agent of air or oxygen, the combustion temperature, the combustion time and the like and cannot be limited with nonambiguity. Normally, the oxygen concentration is high and further, at high temperatures the concentrations of $Cl_2$ and $NO_x$, are increased and those of CO, gaseous organic compounds and carbides are decreased and the oxygen concentration is low while at low temperatures the reverse is the case.

This acid gas as such can be contacted with water to allow hydrogen chloride to be absorbed in water but before this contact with water, a reducing agent can be added to the acid gas to reduce oxidative gas components.

The reducing agent to be used is preferably a compound which gasifies in a high temperature atmosphere and includes, for example, a nitrogen based compound such as ammonia, urea, hydroxylamine, hydrazine, an alkanolamine and an ethyleneamine; an oxygen-containing hydrocarbon compound such as formic acid, oxalic acid, ethylene glycol and a glucose; a sulfur based compound such as hydrogen sulfide, sulfurous acid and an $SO_2$ gas; and an $H_2$ gas, and of these compounds, the nitrogen based compound can easily remove the oxidative gas by reduction and thus, is preferably used. These reducing agents can be used singly or as a mixture of two or more reducing agents.

The amount of the reducing agent to be used can be a sufficient amount to reduce the oxidative gas components which enables the judgement of the oxidation-reduction potential of a crude hydrogen chloride aqueous solution to be obtained by contacting the acid gas having been added with the reducing agent with water to allow hydrogen chloride to be absorbed in water, and the oxidation-reduction potential is preferably not higher than 900 mV. When the oxidation-reduction potential is maintained in this range, substantially all oxidative gas components can be reduced. Furthermore, it is preferred that the reducing agent is added in such an amount as to render the oxidation-reduction potential 600 to 850 mV, more preferably 650 to 800 mV. However, when the reducing agent is directly added to the acid gas, due to the high temperature of the acid gas, part of the reducing agent is consumed by excess oxygen and as the result, the efficiency is sometimes not increased. Thus, in order to advance the oxidation-reduction reaction within a short period of time by increasing the contact efficiency with the acid gas, the reducing agent can be sprayed as such or in the form of an aqueous solution through a spray nozzle or the reducing agent can be introduced in the form of a gas.

The measurement and control of this oxidation-reduction potential are the essential part of the present invention. Effective and efficient performance of this operation can preferably be done by a means capable of automatically controlling the oxidative-reduction potential. A concrete means for controlling the amount of the reducing agent to be added, for example, can automatically or continuously perform sequence control of the amount of the reducing agent to be added with the use of an automatic controller equipped with a control means for controlling the amount of liquid to be supplied by a liquid supply pump or switch-controlling an electromagnetic valve, and can effect control in a preferred narrower range of the amount of the reducing agent. As the result, the reduction of oxidative substances can surely be conducted with good reproducibility to constantly produce a crude hydrogen chloride aqueous solution with good quality and, at the same time, the necessary amount of the reducing agent can be minimized. As this oxidation-reduction potential automatic control means, the commercially available one can be employed and further, control means such as conventional pumps and valves can be combined with control means equipped with a suitable control system.

The oxidation-reduction potential can easily be measured by a commercially available measuring device and electrodes. The value of this oxidation-reduction potential varies depending the measuring temperature selected and the electrodes used and accordingly, in the present invention, as shown in the Examples, when the measurement is conducted at a measuring temperature of 25° C. with the use of a platinum electrode and a saturated silver chloride electrode, the sum of the measured value and a single electrode potential of 199 mV is regarded as the oxidation-reduction potential and this value is shown.

Then, in the present invention, the acid gas obtained by the combustion of chlorine based waste or the above described gas obtained by adding the reducing agent to the acid gas is contacted with water to obtain a crude hydrogen chloride aqueous solution but before this contact with water, the gas can be washed with water or hydrochloric acid by providing a washing column to eliminate carbides and foreign substances such as carbides, inorganic substances from the combustion step.

The contact of the acid gas or the gas having been added with a reducing agent with water can suitably be conducted by normally employed gas-liquid contact equipment. For example, a packed column system, a plate column system, a spray column system, an ejector system, a bubble tower system and the like can be mentioned. In the present invention, increase in the contact efficiency between the gas and water and lowering of temperature are devised, and the hydrogen chloride in the gas is absorbed in water to give a crude hydrogen chloride aqueous solution. It is preferred from the standpoint of increasing the absorption efficiency of the hydrogen chloride gas that the gas is countercurrently contacted with water, and this can easily be carried out by the above described plate column system and spray column system.

In contacting the gas with water, the gas to liquid ratio (by volume) varies depending on the composition of the gas and the absorption equipment system and preferably, it is typically 10 to 2,000. The liquid temperature at the time of contact is preferably 30 to 100° C. from practical viewpoints that a high rate of absorption of the gas into water and excess cooling are unnecessary. In the above described temperature range, the absorption efficiency of the hydrogen chloride-containing gas into water is high and the equipment can be made compact.

Furthermore, in the absorption of this hydrogen chloride-containing gas into water, circulation of part of the obtained crude hydrogen chloride aqueous solution to the absorption step can finally produce a highly concentrated crude hydrogen chloride aqueous solution and thus, comes to a preferred process. Further, the reducing agent can also be added in the absorption step of this hydrogen chloride-containing gas into water.

The reducing agent to be used can be any compound capable of reducing oxidative gas components, particularly $Cl_2$, and is not particularly limited, and a reducing agent has high reduction efficiency and ready availability is preferred.

Examples of such a reducing agent can include, first, a sulfur based compound such as a sulfide, a hydrosulfide, sulfur, a sulfite, a hydrogensulfite, a thiosulfate, a sulfurous acid gas and the like and the cation of these salts can be sodium, potassium, calcium, ammonium or the like in addition to a proton. Of these sulfur base compounds, a preferred reducing agent is a sulfide, a bisulfite or a thiosulfate which hardly forms a solid substance such as sulfur during reduction and becomes easier to handle.

The reducing agent further includes a nitrogen based compound such as ammonia, urea, hydroxylamine, hydrazine, an alkanolamine, an ethyleneamine; and an oxygen-containing compound such as formic acid, oxalic acid and a glucose. These compounds have such an effect that the reduced products do not remain in the crude hydrogen chloride aqueous solution in addition to the above described characteristic features. Of these compounds, a nitrogen based compound is preferred and above all, ammonia, hydroxylamine, hydrazine, an alkanolamine and diethylenediamine and ethylenediamine which have a small molecular weight of the ethylenediamines are preferably used.

The above illustrated reducing agents can be used singly or as a mixture of two or more compounds.

In adding the reducing agent, it can be added to the water which is contacted with a hydrogen chloride-containing gas or to a crude hydrogen chloride aqueous solution to be obtained or to a crude hydrogen chloride aqueous solution to be circulated for the absorption of a hydrogen chloride gas therein.

Of these methods, addition of the reducing agent to the crude hydrogen chloride aqueous solution to be circulated removes volatile components to be generated by the oxidation reduction reaction, for example, $N_2$, chloramine and $CO_2$ to be generated in the case of using a nitrogen based compound as the reducing agent together with a discharged gas and thus, is a preferred method. If necessary, this discharged gas is washed with an alkali aqueous solution and the like.

Further, the reducing agent can be added as such or in the form of an aqueous solution. The amount to be added is preferably such that the oxidation-reduction potential of the crude hydrogen chloride aqueous solution after addition of the reducing agent comes to not higher than 900 mV. This potential range of not higher than 900 mV can reduce substantially all oxidative components derived from the oxidative gas components in the crude hydrogen chloride aqueous solution. Moreover, it is preferred to add the reducing agent in an amount so as to render the oxidation-reduction potential of the crude hydrogen chloride aqueous solution in the range of 600 to 850 mV, more preferably in the range of 650 to 800 mV. This operation can be performed by continuously controlling the amount of the reducing agent to be added by using oxidation-reduction potential measuring equipment. Thus, a substantially oxidative component-free, crude hydrogen chloride aqueous solution can be obtained and is withdrawn from absorption equipment. In this instance, water in an amount equal to the amount of the crude hydrogen chloride aqueous solution withdrawn is newly introduced into the absorption equipment. The composition of the crude hydrogen chloride aqueous solution is not particularly limited and typically has a hydrogen chloride concentration of 10 to 30% by weight and, in addition, trace amounts of nitric acid, sulfuric acid, organic substances and floating solids but substantially it does not contain oxidative components such as $Cl_2$.

Then, a purified hydrogen chloride gas can be obtained by distilling the crude hydrogen chloride aqueous solution thus obtained.

The crude hydrogen chloride aqueous solution contains a large amount of the above described impurities in addition to the major component of hydrogen chloride and it sometimes cannot effectively be utilized as such as a hydrogen chloride aqueous solution (hydrochloric acid). On that account, removal of impurities by filtration, adsorption with active carbon and the like can be thought but such means increase the number of steps to become disadvantageous for practical purposes. Then, in the present invention the crude hydrogen chloride aqueous solution is distilled and impurities are removed to obtain a concentrated hydrogen chloride gas of high purity.

As the distillation equipment to be used in distillation, known equipment such as a packed type distillation column and a plate type distillation column can be employed. The operation, when performed in a continuous system, favorably increases productivity and stabilizes the quality of the hydrogen chloride gas to be obtained.

In the distillation, the operational pressure can be either under pressure or under atomosphere or reduced pressure but in order to obtain a high concentration hydrogen chloride gas, pressure distillation is preferred and the distillation is conducted under a pressure condition of typically 0.1 to 3 MPa, preferably 0.2 to 2 MPa. The temperature of the distillation still at the time of distillation can vary depending on the pressure, the hydrogen chloride concentration of the crude hydrogen chloride aqueous solution, the concentration of impurities and the like and thus, it cannot be unconditionally said but the distillation is typically conducted at a temperature of 70 to 200° C.

The number of plates of a distillation column can vary depending on the purity and the concentration of the purified hydrogen chloride gas to be obtained and the composition of the crude hydrogen chloride aqueous solution, and that is typically 5 to 20 of theoretical plate number. Further, it is possible that part of the purified hydrogen chloride gas can be cooled and condensed and then, subjected to refluxing to improve the purity of the purified hydrogen chloride gas. The hydrogen chloride concentration of the distillation column still liquor has been reduced to some extent by recovering hydrogen chloride to come to about 5 to 20% by weight and impurities has been condensed, and it is preferred to purge part of the still liquor. The purged liquor can be either returned to the combustion step or used as the neutralizing agent for the waste liquor which does not require high purity or the like.

From the purified hydrogen chloride gas thus obtained, liquid or solid impurities are fully eliminated and the purified hydrogen chloride gas is substantially water vapor except the major component of hydrogen chloride. And the hydrogen chloride concentration therein varies depending the above described operational conditions and it is preferred that the concentration is adjusted to typically not less than 50% by volume, more preferably not less than 80% by volume, particularly not less than 95% by volume.

This purified hydrogen chloride gas as such can be used as a gas or can be absorbed in pure water to recover and utilize a high purity hydrochloric acid.

The hydrochloric acid to be obtained by the above described method has the quality to be used in industrial applications, as a food additive and as an etcant in electronics/semiconductor related sector. In order to broaden its utilization range and enhance the value added, it is preferred to remove a small amount of the water content present therein. The method of removing water content includes contacting the hydrochloric acid with a dehydrating agent such as concentrated sulfuric acid, zeolite, silica gel and phosphorus pentoxide, and this method can be applied to the purified hydrogen chloride gas to be obtained by the process of the present invention, and an industrially more preferred method comprises cooling the gas to condense water content and remove the water content by an eliminator.

In a more concrete embodiment of cooling operation, cooling can be conducted in a single stage or a multi-stage of two or more stages. Further, the effect of removing moisture can be more increased with decreased cooling temperatures although cooling energy is increased. In addition, the cooling temperature varies depending on the pressure and is typically 5 to 40° C., and it is necessary to note that at low temperatures solidification of the condensate occurs.

The eliminator to be used can be either a collision plate system or a filament system, and the latter is preferably employed due to its higher moisture removal effect. As the filament system, either a bundle of randomly arranged filaments or a folded fabric geometrically woven with filaments can be used, and the latter is preferred to reduce pressure loss and to increase moisture removal effect. With smaller diameters of the filaments or with larger surface areas of the filaments, the moisture removal effect is more increased and thus, it is preferred that the diameter of the filaments is typically 5 μm to 1 mm and such filaments are easily available and have a high moisture removal effect.

The material of the filaments is not particularly limited, and glass fibers having corrosion resistance to purified hydrogen chloride gas, organic polymeric materials such as polyethylene, polypropylene, polyvinyl chloride, polyvinylidene chloride, nylons, fluoroplastics, and metals coated with these resins can be used. Particularly, the purified hydrogen chloride gas to be obtained by the process of the present invention does not substantially contain oxidative components such as $Cl_2$ and thus, filaments of general-purpose, economically advantageous polyethylene and polyvinyl chloride can suitably be used.

The number of plates to be provided in an eliminator can be one or dividedly two or more. Further, a small amount of water or a hydrogen chloride aqueous solution can be sprayed to the site in front of the eliminator installed or into the eliminator. By this spraying, water is to enter the system but the effect of trapping condensate is great and a higher effect than the effect of the entered water can be obtained.

The purified hydrogen chloride gas after removal of moisture only contains trace amounts of water content and is approximately pure, and the concentration of its water content can be made typically not greater than hundreds of ppm, further not greater than tens of ppm, particularly several ppm. The purified hydrogen chloride gas having such a low water content hardly has corrosive properties against metals such as iron and plastics and thus is advantageous to the selection of the material of equipment and becomes industrially favorable. In the measurement of the water content of the purified hydrogen chloride gas, a dew-point hygrometer is normally used. Further, the condensate (hydrogen chloride aqueous solution) can be refluxed to the distillation column or returned to the bottom of the distillation column or to the absorption step of the acid gas.

This purified hydrogen chloride gas as such can broadly and effectively be used in the oxychlorination reaction in the production of dichloroethane, as a feedstock for the production of high purity chlorides, as a food additive, as an etchant in electronic semiconductor-related sector and the like.

When it is necessary to completely eliminate trace amounts of the water content in the purified hydrogen chloride gas after removal of moisture, the purified hydrogen chloride gas can be contacted with the above described dehydrating agent such as concentrated sulfuric acid, zeolite, silica gel and phosphorus pentoxide. In this instance, the water content to be eliminated is trace amounts and accordingly, the necessary amount of the dehydrating agent can be minimized and is economical and industrial. The purified hydrogen chloride gas after elimination of water is non-corrosive and advantageous in the aspects of materials of equipment, operating characteristics and handling properties. Accordingly, its applications can be broadened.

The purified hydrogen chloride gas after removal of moisture or after elimination of water can be compressed by a compressor to prepare a pressurized hydrogen chloride gas or a liquefied hydrogen chloride. In this instance, transportation facilities including piping and storage facilities can be made compact and are extremely effective from an industrial viewpoint. The preparation of this pressurized hydrogen chloride gas or liquefied hydrogen chloride further broadens its use and enables filling in bombs. Particularly, such hydrogen chlorides are effectively utilized in the oxychlorination reaction for producing dichloroethane in the vinyl chloride monomer production plant which consumes a large amount of hydrogen chloride. In this use, the liquefied hydrogen chloride can inhibit formation of by-products due its high purity.

As the materials of equipment, general-purpose metals such as iron, general-purpose plastics such as polyethylene and polyvinyl chloride and furthermore, lined materials in consideration of pressure resistance can be adopted and highly economical. Further, the pressure at the time of filling and transportation varies depending on the temperature and is operated typically at not less than 0.2 MPa for the pressurized hydrogen chloride gas and typically at not less than 1 MPa for the liquefied hydrogen chloride. In addition, in compressing the purified hydrogen chloride gas, a large quantity of heat is evolved and thus, it is necessary to remove heat by cooling.

EXAMPLES

The present invention will now be explained in more detail with reference to examples which should not be construed to limit the present invention. Further, "part" and "%" shown in the examples and the comparative examples are based on weight.

(1) Measurement of Oxidation-Reduction Potential

Oxidation-reduction potential measuring electrodes were set at oxidation-reduction potential measuring equipment ODIC-7, manufactured by TOA Electronics Ltd. and measurement was conducted at 25° C. As the electrodes, a composite electrode (PS 8250) of a platinum electrode with a saturated silver chloride electrode was used.

(2) Quantitative Analysis of Chlorine by o-Tolidine Method

A predetermined amount of the aqueous solution obtained by allowing a hydrochloric acid aqueous solution or a hydrogen chloride gas to be absorbed in pure water was sampled, and thereto 5 ml of a 5% o-tolidine hydrochloric aqueous solution were added and mixed and then, pure water was added thereto to form a sample of a predetermined volume. The sample thus prepared was subjected to colorimetry in a 10 mm cell with a wavelength of 438 nm. Separately, a calibration curve showing the relationship between the chlorine concentration and absorbance was obtained with the use of a reference solution prepared from sodium hypochlorite and a guaranteed reagent hydrochloric acid, and from this calibration curve the chlorine concentration in the sample was obtained. Further, the effective chlorine concentration in the sodium hydrochlorite was regarded as the chlorine concentration.

Example 1

A chlorine based organic waste liquor (C:28%, Cl:58%) from a dichloroethane production plant was sprayed from a nozzle with pressurized air into a horizontal incinerator to effect combustion. A combustion gas, i.e., an acid gas was quenched by being sprayed with water thereon, and introduced into a hydrogen chloride absorber. Absorption was continuously performed with the use of 10-stage glass Oldershow equipment. The quenched acid gas was fed to the lowest part of the absorption column and a 10% hydrochloric acid prepared by adding water to a crude hydrogen chloride aqueous solution was fed to the top of the column. From the bottom of the column, a 20% crude hydrogen chloride aqueous solution of 40° C. having absorbed a hydrogen chloride gas could be obtained. This crude hydrogen chloride aqueous solution showed a pale yellow color and had a $Cl_2$ concentration of 30 ppm measured by the above described o-tolidine calorimetric analysis. Further, the oxidation-reduction potential of this crude hydrogen chloride aqueous solution measured by the above described method was 1,150 mV.

Then, 1.4 parts of a 1% hydrazine aqueous solution were added to 1,000 parts of the obtained crude hydrogen chloride aqueous solution. Upon addition of this hydrazine aqueous solution, simultaneously the oxidation-reduction potential was quickly decreased to come to 730 mV and at this time, no $Cl_2$ was detected by the o-tolidine calorimetric analysis and thus, the amount of $Cl_2$ was not greater than the detection limit (0.1 ppm).

Then, the crude hydrogen chloride aqueous solution after reduction was subjected to pressure distillation with a glass-packed distillation column having a theoretical plate number of 8. In this instance, the reflux ratio (R/D) of a reflux condenser was set at 1.0. From the top of the distillation column was obtained a purified hydrogen chloride gas which was then maintained at 20° C. and introduced into a gas absorber filled with pure water. When the concentration of the hydrogen chloride in the bottom liquor of the distillation column reached 10%, the distillation was completed and at this time, a 35% high purity hydrochloric acid was obtained in the gas absorber. With this hydrochloric acid, metallic impurities, organic impurities and $Cl_2$ were analyzed by ICP (detection limit: 1 ppm), a TOC meter (detection limit: 1 ppm) and the o-tolidine calorimetric analysis, respectively. None of them were detected and thus, it was confirmed that the hydrochloric acid was an extremely high purity hydrochloric acid.

Example 2

To 1,000 parts of the crude hydrogen chloride aqueous solution obtained in Example 1 were added 12 parts of a 1% hydroxylamine hydrochloride ($NH_2OH·HCl$) aqueous solution. Upon addition of the hydroxylamine hydrochloride aqueous solution, simultaneously the oxidation-reduction potential was decreased to 710 mV and at this time, no $Cl_2$ was detected by the o-tolidine colorimetric analysis.

Then, this solution after reduction was subjected to pressure distillation in the same equipment under the same conditions as in Example 1 to obtain a hydrogen chloride solution gas from the top of the distillation column which was then absorbed in pure water in the same manner as in Example 1 to obtain a 35% high purity hydrochloric acid. In this hydrochloric acid, none of metallic impurities, organic impurities and $Cl_2$ were detected and thus, it was confirmed that this hydrochloric acid was an extremely high purity hydrochloric acid.

Example 3

To 1,000 parts of the crude hydrogen chloride aqueous solution obtained in Example 1 were added 25 parts of a 2.5% sodium thiosulfate ($Na_2S_2O_3·5H_2O$) aqueous solution. Upon addition of the sodium thiosulfate aqueous solution, simultaneously the reduction reaction proceeded and the oxidation-reduction potential was decreased from 1,159 mV to 502 mV, and no $Cl_2$ was detected by the o-tolidine colorimetric analysis and thus, it was confirmed that the reduction fully proceeded. Then, the amount of the sodium thiosulfate aqueous solution was reduced to 9.6 parts which were then added to 1,000 parts of the above described crude hydrogen chloride aqueous solution. As the result, the reduction reaction proceeded in the same manner and the oxidation-reduction potential was decreased from 1,159 mV to 663 mV, and no $Cl_2$ was detected by the o-tolidine colorimetric analysis.

Then, each of the crude hydrogen chloride aqueous solutions after reduction was subjected to pressure distillation in the same equipment under the same conditions as in Example 1 to obtain a hydrogen chloride solution from the top of the distillation column which was then absorbed in pure water in the same manner as in Example 1 to obtain a 35% high purity hydrochloric acid. In the hydrochloric acid thus obtained, none of metallic impurities, organic impurities and $Cl_2$ were detected and thus, it was confirmed that the hydrochloric acid was an extremely high purity hydrochloric acid.

Comparative Example 1

The same procedure as in Example 1 was repeated except that the hydrazine aqueous solution of the reducing agent was not used.

As the result, the obtained crude hydrogen chloride aqueous solution had an oxidation-reduction potential of 1,150 mV, the hydrochloric acid obtained in the gas absorber showed an extremely dark yellow color, and the $Cl_2$ concentration was as comparatively high as 90 ppm.

Comparative Example 2

To 1,000 parts of the crude hydrogen chloride aqueous solution obtained in Example 1 was added 0.7 part of a 1% hydroxylamine hydrochloride ($NH_2OH·HCl$) aqueous solution. The oxidation-reduction potential was decreased to stop at 950 mV.

Then, this solution after reduction was subjected to pressure distillation in the same equipment under the same conditions as in Example 1 to obtain a hydrogen chloride solution gas from the top of the distillation column which was then absorbed in pure water in the same manner as in Example 1 to obtain a 35% hydrochloric acid. This hydrochloric acid showed a pale yellow color and the $Cl_2$ concentration was 13 ppm.

According to the present invention, a useful high purity hydrogen chloride can effectively and efficiently be recovered from chlorine based waste. The effects of the present invention will be enumerated below.

(1) From chlorine based waste, a useful hydrogen chloride can be recovered and this is meaningful from the standpoint of preservation of environment and utilization of resources.

(2) The process is an industrial process which is comparatively simple and can easily be automated.

(3) Independently of the type of the chlorine based waste, a high purity hydrogen chloride can constantly be recovered.

(4) The hydrogen chloride to be recovered is of high purity and accordingly, can be widely utilized in the production of inorganic and organic chlorides and as an food additive, an etchant in electronics/semiconductor sector and the like.

(5) The corrosive properties of the recovered hydrogen chloride gas are reduced and accordingly, iron and general-purpose plastics can be used as the materials of the equipment.

(6) The recovered hydrogen chloride can be used as the feedstock in the oxychlorination reaction for the production of a vinyl chloride monomer.

(7) The recovered hydrogen chloride can be converted into a liquefied hydrochloric acid, and its transportation and storage facilities can be made compact.

While the present invention has been described in the foregoing fashion, it is to be understood that the invention is not limited thereby, but may be varied in many other ways. Such variations are not to be regarded as a departure from the spirit and scope of the invention, and all such modifications as would be obvious to one skilled in the art are intended to be included within the scope of the appended claims.

What is claimed is:

1. A method for recovering hydrogen chloride from chlorine based waste which comprises adding water and a reducing agent to an acid gas obtained by the combustion of chlorine based waste to effect reaction to obtain a crude hydrogen chloride aqueous solution having an oxidation-reduction potential of 600 to 850 mV and then, distilling the crude hydrogen chloride aqueous solution to obtain a purified hydrogen chloride gas.

2. The method for recovering hydrogen chloride from chlorine based waste of claim 1, wherein an oxidation-reduction potential automatic control means for measuring the oxidation-reduction potential of the crude hydrogen chloride aqueous solution and automatically controlling the amount of the reducing agent is used to control the oxidation-reduction potential of 600 to 850 mV.

3. The method for recovering hydrogen chloride from chlorine based waste of claim 1, wherein the oxidation-reduction potential of the crude hydrogen chloride aqueous solution is 650 to 800 mV.

4. The method for recovering hydrogen chloride from chlorine based waste of claim 1, wherein before addition of the reducing agent, the acid gas is contacted with water.

5. The method for recovering hydrogen chloride from chlorine based waste of claim 1, wherein after addition of the reducing agent to the acid gas, water is added.

6. The method for recovering hydrogen chloride from chlorine based waste of claim 1, wherein a reducing agent-containing aqueous solution is added to the acid gas.

7. The method for recovering hydrogen chloride from chlorine based waste of claim 1, wherein the reducing agent is a sulfur based compound and/or a nitrogen based compound.

8. The method for recovering hydrogen chloride from chlorine based waste of claim 1, comprising cooling the obtained purified chlorine gas, and removing moisture from it by an eliminator.

9. The method for recovering hydrogen chloride from chlorine based waste of claim 8, further comprising compressing the purified hydrogen chloride gas after removal of moisture to obtain a pressurized hydrogen chloride gas or a liquefied hydrogen chloride gas.

10. The method for recovering hydrogen chloride from chlorine based waste of claim 1, comprising contacting the purified hydrogen chloride gas with water to obtain a purified hydrogen chloride aqueous solution.

11. A method for recovering hydrogen chloride from chlorine based waste which comprises adding water and a reducing agent to an gas obtained by the combustion of chlorine based waste to effect reaction to obtain a crude hydrogen chloride aqueous solution having an oxidation-reduction potential of 600 to 850 mV by using an oxidation-reduction potential automatic control means for measuring the oxidation-reduction potential of the crude hydrogen chloride aqueous solution and automatically controlling the amount of the reducing agent and then, pressure distilling the crude hydrogen chloride aqueous solution to obtain an purified hydrogen chloride gas.

* * * * *